US010967119B1

(12) United States Patent
Bilal

(10) Patent No.: US 10,967,119 B1
(45) Date of Patent: Apr. 6, 2021

(54) WEARABLE MEDICATION INJECTING DEVICE

(71) Applicant: Azizi Bilal, Brooklyn, NY (US)

(72) Inventor: Azizi Bilal, Brooklyn, NY (US)

( * ) Notice: Subject to any disclaimer, the term of this patent is extended or adjusted under 35 U.S.C. 154(b) by 115 days.

(21) Appl. No.: 16/371,738

(22) Filed: Apr. 1, 2019

(51) Int. Cl.
*A61M 5/142* (2006.01)
*A61M 5/145* (2006.01)
*A61M 5/00* (2006.01)
*A61M 5/158* (2006.01)
*A61M 37/00* (2006.01)

(52) U.S. Cl.
CPC ...... *A61M 5/14244* (2013.01); *A61M 5/1456* (2013.01); *A61M 2005/005* (2013.01); *A61M 2005/14208* (2013.01); *A61M 2005/14268* (2013.01); *A61M 2005/14506* (2013.01); *A61M 2005/1585* (2013.01); *A61M 2037/0023* (2013.01); *A61M 2205/3569* (2013.01); *A61M 2205/3584* (2013.01); *A61M 2205/502* (2013.01); *A61M 2209/088* (2013.01)

(58) Field of Classification Search
CPC ............ A61M 5/14244; A61M 5/1456; A61M 2205/3569; A61M 2209/088; A61M 2037/0023; A61M 2005/14506; A61M 2205/502; A61M 2005/14268; A61M 2005/1585; A61M 2005/005; A61M 2205/3584
See application file for complete search history.

(56) References Cited

U.S. PATENT DOCUMENTS

| 5,569,186 | A | 10/1996 | Lord et al. |
| 6,641,533 | B2 | 11/2003 | Causey, III et al. |
| 6,645,177 | B1 * | 11/2003 | Shearn ................ A61M 5/1456 604/155 |
| 8,192,394 | B2 | 6/2012 | Estes et al. |
| 8,597,570 | B2 | 12/2013 | Terashima et al. |
| 8,663,201 | B2 | 3/2014 | Hill et al. |
| 8,933,108 | B2 | 1/2015 | Cao et al. |
| 9,011,376 | B2 | 4/2015 | Genosar et al. |
| 9,047,398 | B2 | 6/2015 | Kaufmann et al. |
| 9,050,297 | B2 | 6/2015 | Chakraborty et al. |

(Continued)

*Primary Examiner* — Bhisma Mehta
*Assistant Examiner* — Robert F Allen
(74) *Attorney, Agent, or Firm* — Goldstein Law Offices, P.C.

(57) ABSTRACT

A wearable medication injecting device which is worn on a patient's body and adapted to automatically administer medication to the patient via a scheduled injection, the device comprising a detachable medication module containing the medication and a needle, a medication injection assembly having a mounting plate with at least one attachment point for removably engaging the detachable medication module, and a band which secures the mounting plate against the patient's skin surface. The needle is adapted to pass through the mounting plate to penetrate the skin surface and deliver the medication. Replacing the detachable medication module both replenishes the medication and replaces the needle, and attaching additional detachable medication modules allows a second medication to be simultaneously administered. A user control device is adapted to wirelessly communicate with the medication injection assembly to control the scheduled injections and convey device status alerts to a user.

20 Claims, 16 Drawing Sheets

(56) References Cited

U.S. PATENT DOCUMENTS

| | | | |
|---|---|---|---|
| 9,056,167 B2 | 6/2015 | Pesach et al. | |
| 9,061,059 B2 | 6/2015 | Chakraborty et al. | |
| 2012/0078216 A1* | 3/2012 | Smith | A61M 5/1452 |
| | | | 604/500 |
| 2012/0185267 A1* | 7/2012 | Kamen | A61B 5/0024 |
| | | | 705/2 |
| 2017/0216524 A1 | 8/2017 | Haider et al. | |
| 2017/0304540 A1 | 10/2017 | Despa et al. | |
| 2017/0333623 A1* | 11/2017 | Kamen | A61M 5/16827 |
| 2018/0193563 A1* | 7/2018 | Krasnow | A61M 5/3153 |
| 2018/0264189 A1 | 9/2018 | Michaud et al. | |
| 2020/0121558 A1* | 4/2020 | Lanigan | A61J 1/1481 |

* cited by examiner

WEARABLE MEDICATION INJECTING DEVICE

TECHNICAL FIELD

The present disclosure relates generally to a device for administering medication to a patient via injection. More particularly, the present disclosure relates to a wearable medication injecting device which contains a quantity of medication which is automatically administered to the patient at an appropriate dose time.

BACKGROUND

Many patients who suffer from chronic disease are required to take medication. Unfortunately, a large percentage of patients do not take their medications properly in accordance with their prescriptions, and 50% of patients will actually stop taking their medications altogether within the first year of the medication being prescribed. A majority of these patients are unable to take their medications as prescribed due to factors such as forgetfulness and procrastination, confusion over complex medication regimens, as well as anxiety—particularly in the case of medications administered through injections. Certain patients are required to take medication at odd times or late at night, increasing the likelihood of missing a dose. For patients with serious illnesses, the consequences of missing a dose may be life-threatening.

A wide variety of devices for administering medications by injection may be found within the prior art. Certain devices are worn by the patient and use the assistance of a computer to schedule injections, which are particularly valuable for patients at risk of missing doses which must be administered during sleeping hours. However, many of these devices administer medication via a catheter which remains painfully embedded in the patient's skin. The catheter must be regularly transferred to a new location on the patient's body, and there is a risk of the catheter site becoming infected. Furthermore, the devices within the prior art are only capable of administering one medication.

Therefore, an urgent need exists for a device which can be worn on the patient's body, which is capable of automatically administering one or more medications via scheduled injections, without the use of embedded needles or catheters.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a wearable device which allows injections of medication to be automatically administered to a patient. Accordingly, the present disclosure provides a wearable medication injecting device comprising a medication injection assembly containing medication and a needle. The wearable medication injecting device is adapted to be secured to a limb of the patient in contact with the patient's skin surface via an elastic band, and the medication is automatically administered to the patient at an appropriate dose time.

It is another aspect of an example embodiment in the present disclosure to provide a wearable device which allows the medication to be easily replenished and for the needle to be replaced after each injection. Accordingly, the wearable medication injecting device further comprises a detachable medication module which houses the needle and is further adapted to store the medication. The mounting panel further has an attachment point adapted to allow the detachable medication module to be removably engaged within. Replacement of the detachable medication module with a new module replaces the needle and replenishes the medication.

It is yet another aspect of an example embodiment in the present disclosure to provide a wearable device which allows multiple injections to be administered to the patient. Accordingly, the mounting panel of the medication injection assembly has multiple attachment points, each adapted to hold a separate detachable medication module, allowing an injection to be administered using each of the detachable medication modules.

It is a further aspect of an example embodiment in the present disclosure to provide a wearable device which is wirelessly controlled and monitored by a separate control device. Accordingly, the present disclosure provides a user control device which is adapted to wirelessly communicate with the wearable medication injecting device. The user control device allows a user to set a dose schedule by which the injections are automatically administered, and is further adapted to relay the status of the wearable medication injecting device to the user.

It is yet a further aspect of an example embodiment in the present disclosure to provide a wearable medication injecting device which allows for the simultaneous administering of more than one medication to the patient. Accordingly, each detachable medication module may contain a different medication, and the user control device is further adapted to administer each medication according to a separate dose schedule.

It is still a further aspect of an example embodiment in the present disclosure to provide a wearable medication injecting device capable of accepting a standard syringe. Accordingly, the detachable medication module has medication housing adapted to receive a syringe with a plunger, and further has a medication transport line adapted to carry the medication from the syringe to the needle.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
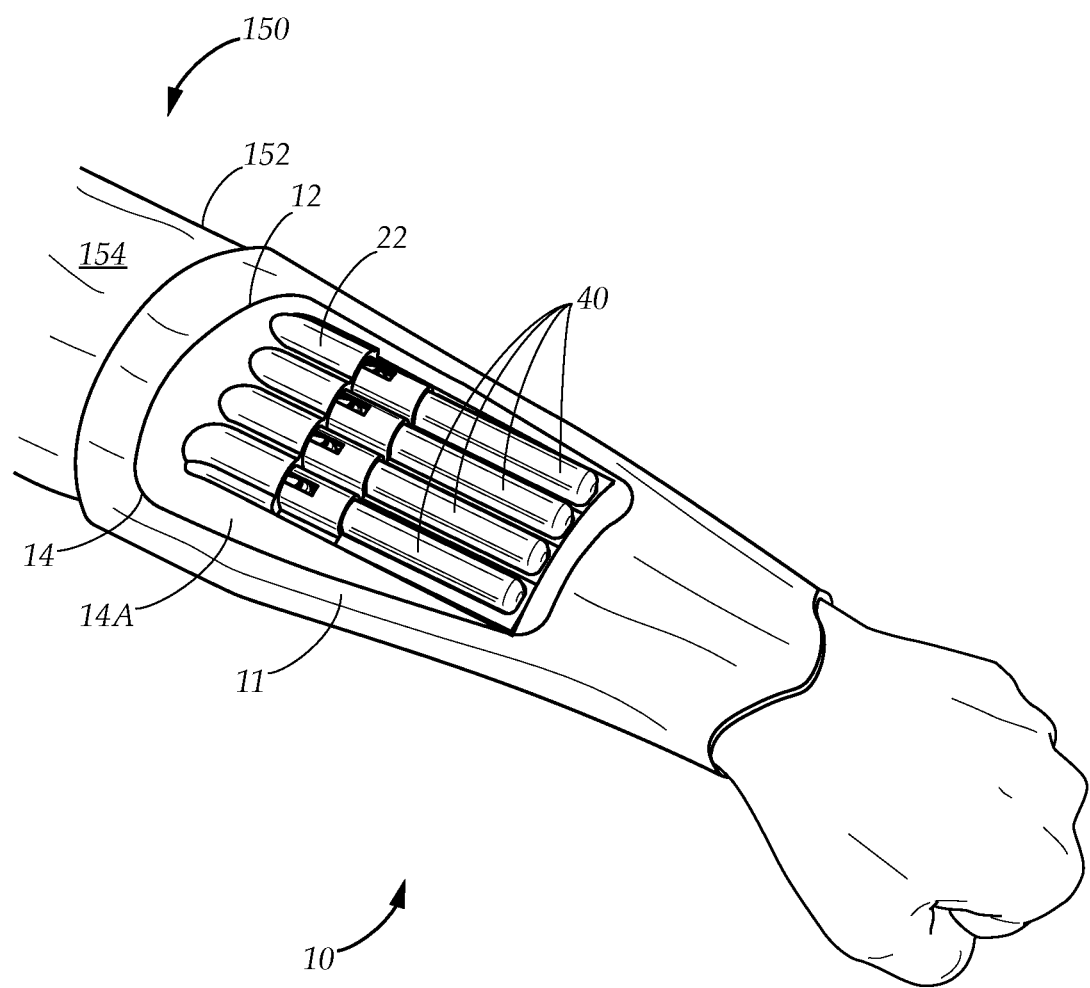
FIG. 1 is a diagrammatical perspective view of a wearable medication injecting device worn by a patient on the patient's forearm, comprising a medication injection assembly and a band, in accordance with an embodiment of the present disclosure.
Figure 4:
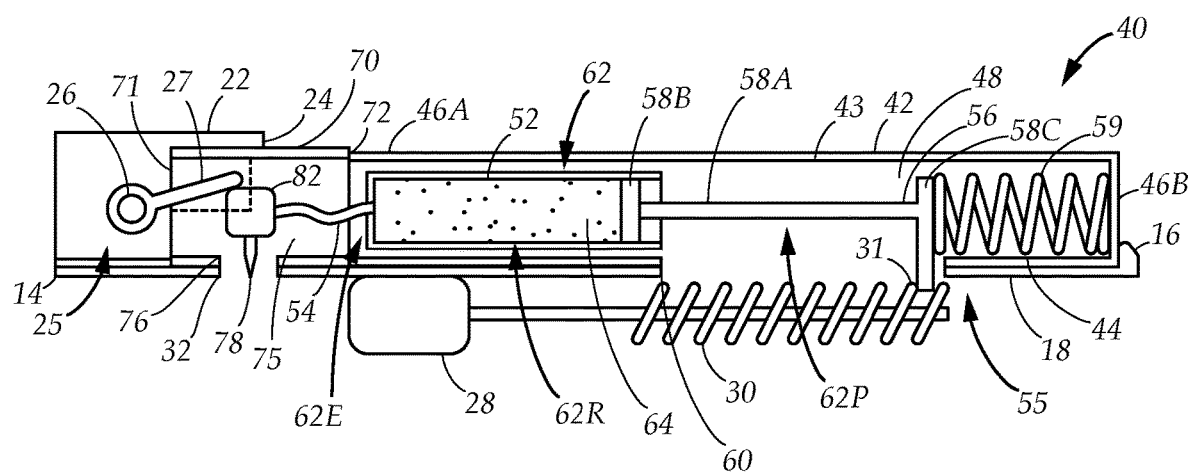
FIG. 4 is a diagrammatical cross section view of the detachable medication module connected to the attachment point, showing a medication housing interior containing a reservoir holding medication and an injection plunger, along with a needle actuator motor and needle actuator arm for lowering the needle head and needle through the needle opening, and an injection actuation motor with a worm gear for advancing the plunger to deliver medication through the needle, in accordance with an embodiment of the present disclosure.

FIG. 1 illustrates a wearable medication injecting device 10 comprising a medication injection assembly 12, at least one detachable medication module 40, and a band 11 to which the medication injection assembly 12 is secured. The band 11 may be formed from a loop of elastic cloth adapted to wrap around a limb of a patient 150 to secure the wearable medication injecting device in contact with the patient's skin surface 154. In one embodiment, the wearable medication injecting device 10 may be worn around a forearm 152 of the patient 150. Referring to FIG. 4 along with FIG. 1, the medication injection assembly 12 is adapted to inject a dose of liquid medication 64 stored within the detachable medication module 40 through the patient's skin surface 154 using a needle 78. The detachable medication module 40 may be removed and replaced, thereby both replenishing the medication 64 stored within and replacing the needle 78.

Figure 2A:
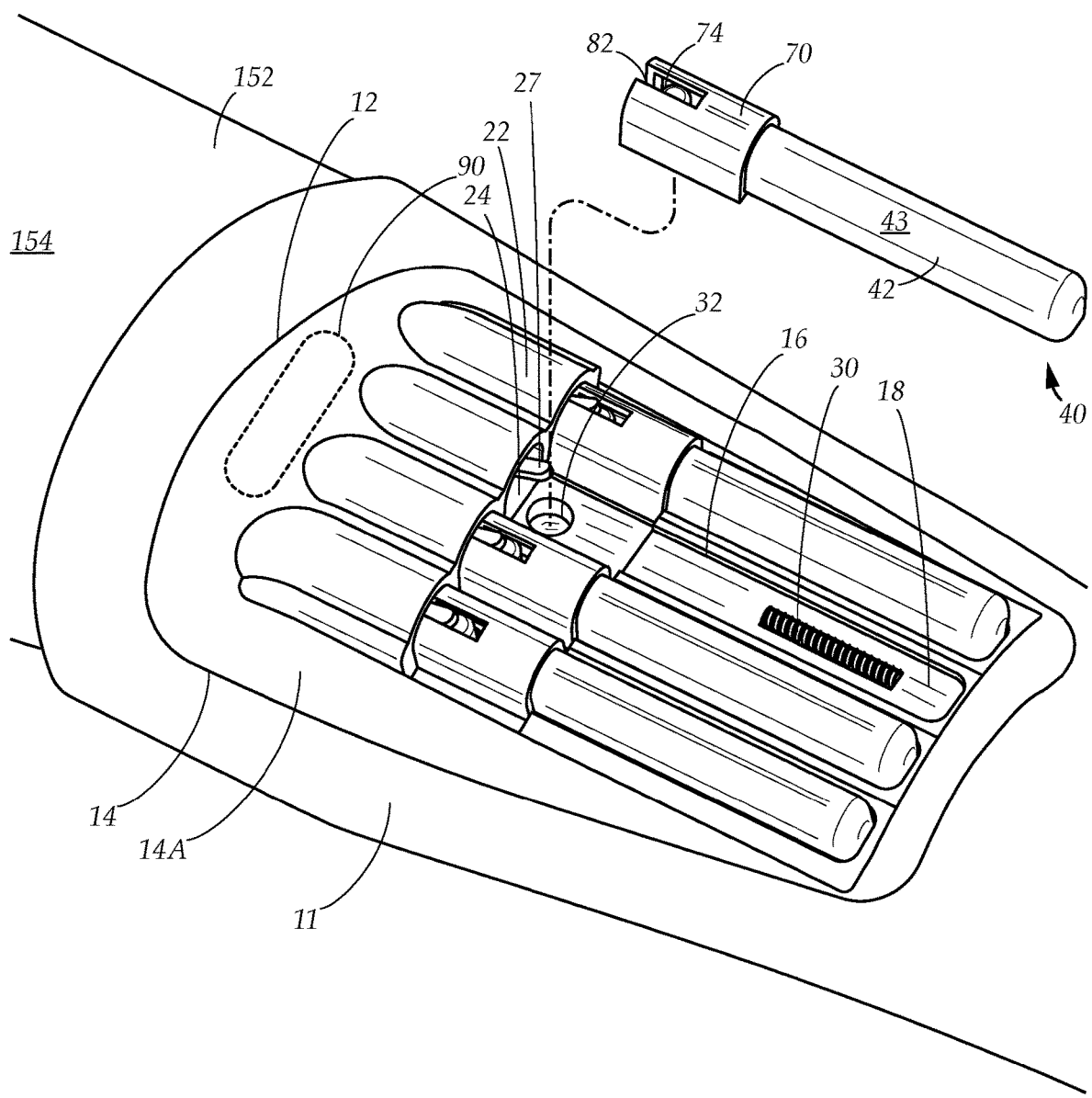
FIG. 2A is a diagrammatical perspective view of the wearable medication injecting device showing a mounting panel having a plurality of attachment points each adapted to receive a detachable medication module, in accordance with an embodiment of the present disclosure.
Figure 2B:
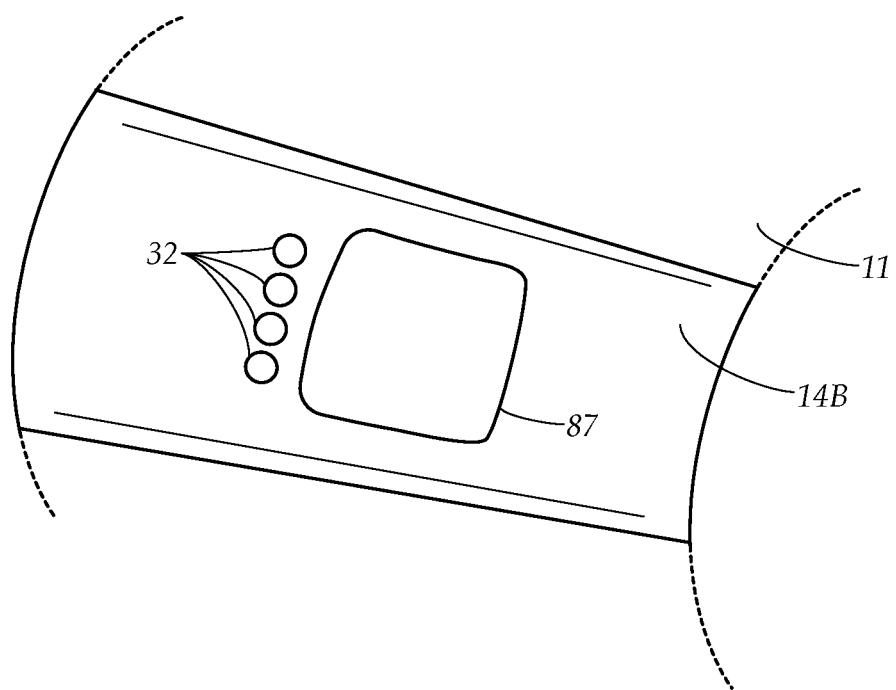
FIG. 2B is a diagrammatical perspective view of the wearable medication injecting device showing a mounting panel inner face adapted to rest against the patient's skin, along with a plurality of injection apertures and a device contact sensor, in accordance with an embodiment of the present disclosure.
Figure 7A:
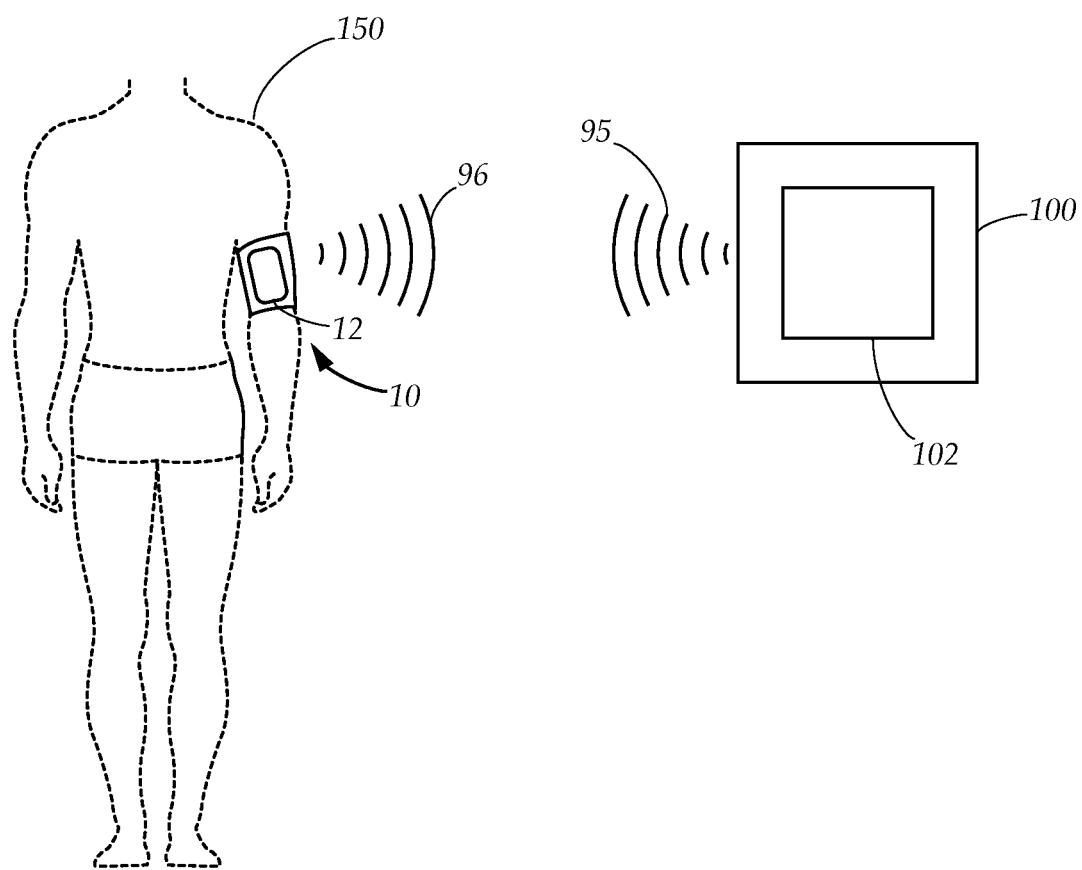
FIG. 7A is a block diagram depicting the wearable medication injecting device communicating wirelessly with a user control device, in accordance with an embodiment of the present disclosure.

Operation of the wearable medication injecting device 10 is wirelessly controlled using a user control device 100 as shown in FIG. 7A, allowing injections to be performed automatically without intervention on the part of the patient 150. Referring to FIGS. 2A-B, the medication injection assembly 12 has a mounting panel 14 having an upper face 14A and an inner face 14B. The upper face 14A has at least one attachment point 16 adapted to receive the detachable medication module 40, while the inner face 14B is adapted to rest against the skin surface 154. The mounting panel 14 provides structural rigidity to offset the elasticity and flexibility of the band 11, and may be curved to accommodate the patient's limb.

Referring to FIG. 4 and FIGS. 3A-C simultaneously, the detachable medication module has a medication housing 42 and a needle housing 70. The medication housing 42 has a medication housing first end 46A, a distally oriented mediation housing second end 46B, and a medication housing shell 43 formed therebetween. The medication housing shell 43 has a medication housing bottom surface 44, and a medication housing interior space 48 enclosing a medication reservoir 52 adapted to contain the medication 64. The needle housing 70 has a needle housing first end 71, an open end 72 positioned opposite thereof, a needle housing bottom surface 73, and a needle housing interior space 75. The needle housing interior space 75 encloses a needle head 82, and the needle 78 is held in place upon the needle head 82 such that the needle 78 points downwardly towards a needle opening 76 formed in the needle housing bottom surface 73. The needle head 82 is adapted to move downwardly toward the needle opening 76, allowing the needle 78 to pass therethrough. In a preferred embodiment, the medication housing first end 46A is attached to the needle housing open end 72, and a medication transport line 54 connects the medication reservoir 52 with the needle head 82 and allows the medication 64 to be transported from the medication reservoir 52 to the needle 78. The medication transport line 54 may be a tube, pipe, or other conduit by which fluids may travel.

In a preferred embodiment, the detachable medication module 40 further has an injection plunger 56 having a plunger head 58B, a distally oriented plunger flange 58C, and a plunger shaft 58A extending therebetween. The medication reservoir 52 may be cylindrically shaped, and is adapted to form a sealed engagement with the plunger head 58B. By advancing the injection plunger 56, the plunger head 58B is expelled out of the medication reservoir 52 and is carried to the needle 78 via the medication transport line 54. Furthermore, the medication housing bottom surface 44 may have a plunger actuation slot 60 which exposes the injection plunger 56 within the medication housing interior space 48.

Figure 5A:
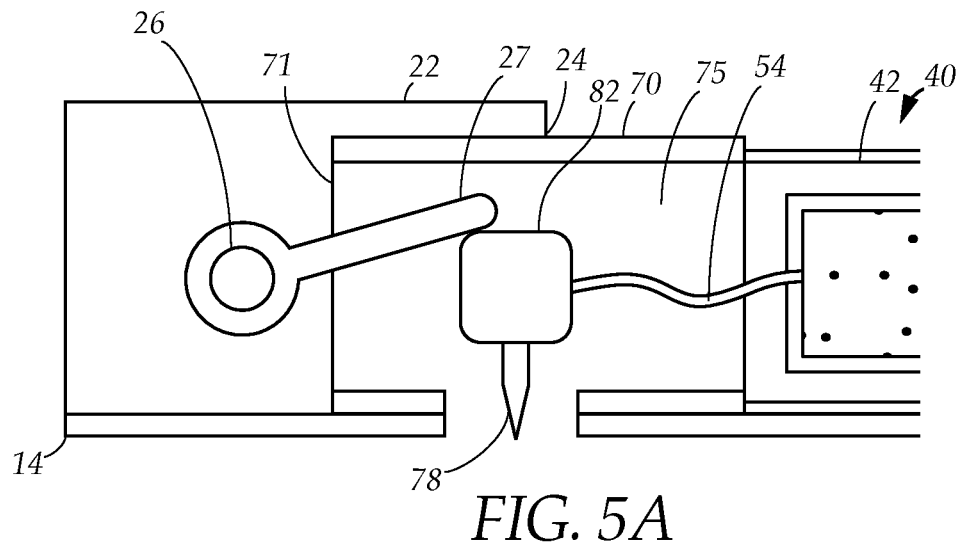
FIG. 5A is a diagrammatical cross section view of the needle housing, showing a medication transport line which allows medication to flow from the reservoir through the needle, in accordance with an embodiment of the present disclosure.
Figure 5B:
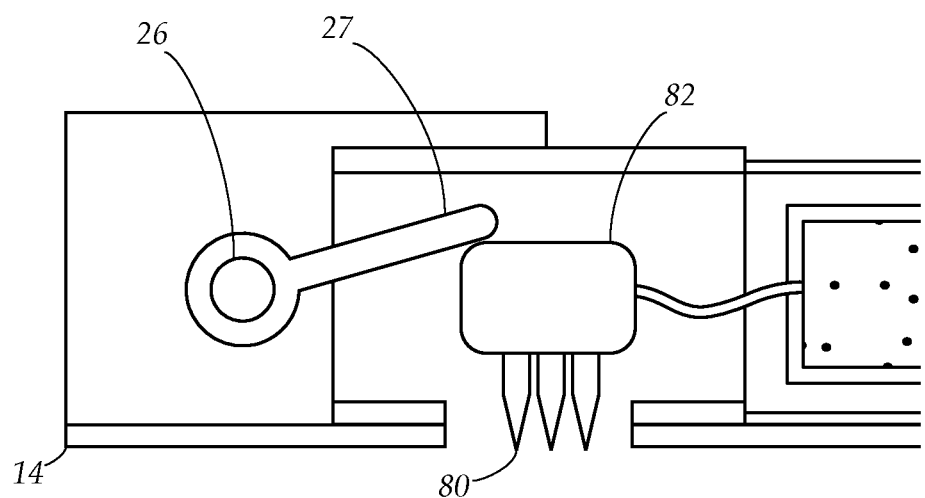
FIG. 5B is a diagrammatical cross section view of the needle housing, showing an alternate needle head with a microneedle array, in accordance with an embodiment of the present disclosure.
Figure 5C:
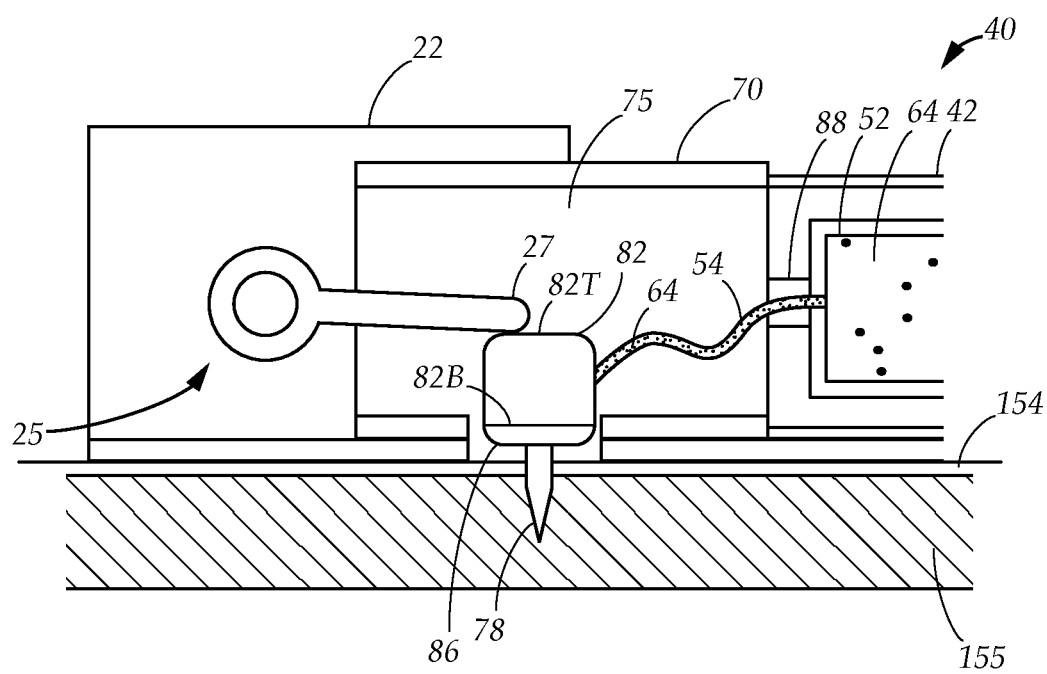
FIG. 5C is a diagrammatical cross section view of the needle housing, showing the needle penetrating the skin surface of the patient to deliver the medication to subcutaneous tissue, in accordance with an embodiment of the present disclosure.

Referring to FIG. 2A and FIG. 5C while continuing to refer to FIG. 4 and FIGS. 3A-C, the detachable medication module 40 is adapted to be removably engaged within the attachment point 16 of the mounting panel 14, thus allowing the medication 64 to be replenished upon depletion of the medication reservoir 52 by simply replacing the depleted detachable medication module 40 with another module.

In a preferred embodiment, the attachment point 16 is elongated in shape to substantially match the needle housing bottom surface 73 of the detachable medication module 40. The medication injection assembly 12 further has a needle actuation mechanism 25 and an injection actuation mechanism 55 positioned at the attachment point 16, adapted to actuate the needle head 82 and the injection plunger 56 respectively. Furthermore, the injection aperture 32 is positioned to align with the needle opening 76 when the detachable medication module 40 is engaged within the attachment point 16, allowing the needle 78 to pass through the mounting panel 14 to penetrate the skin surface 154.

Figure 2C:
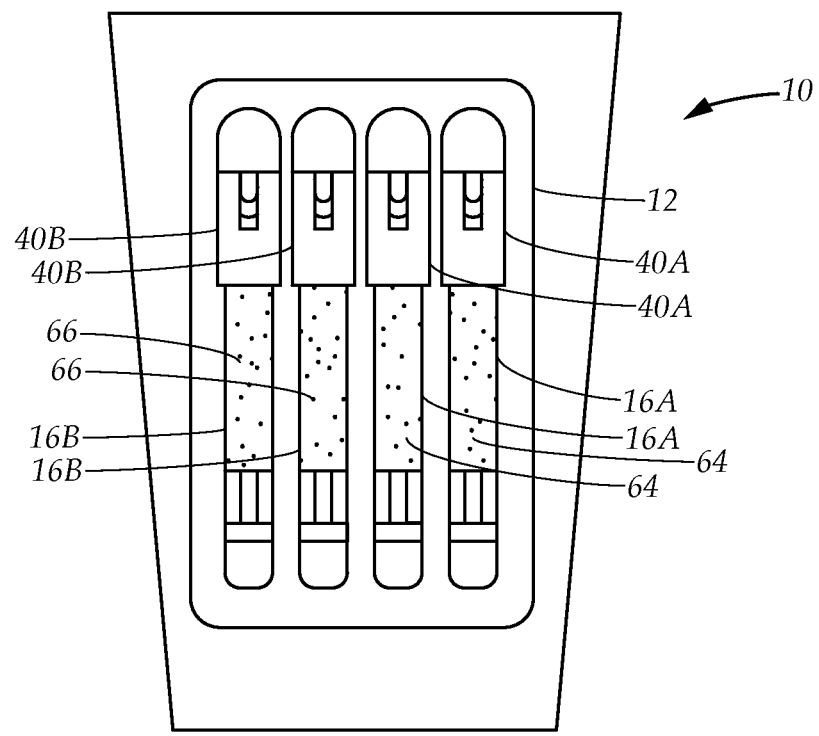
FIG. 2C is a diagrammatical top view of the wearable medication injecting device, depicting a second detachable medication module storing a second medication which is engaged within a second attachment point, in accordance with an embodiment of the present disclosure.
Figure 3A:
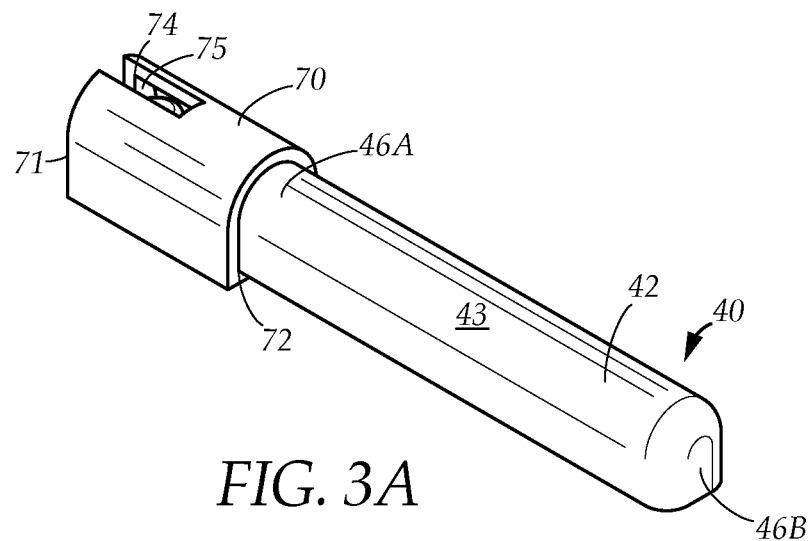
FIG. 3A is a diagrammatical perspective view of the detachable medication module comprising a medication housing and a needle housing, in accordance with an embodiment of the present disclosure.
Figure 3B:
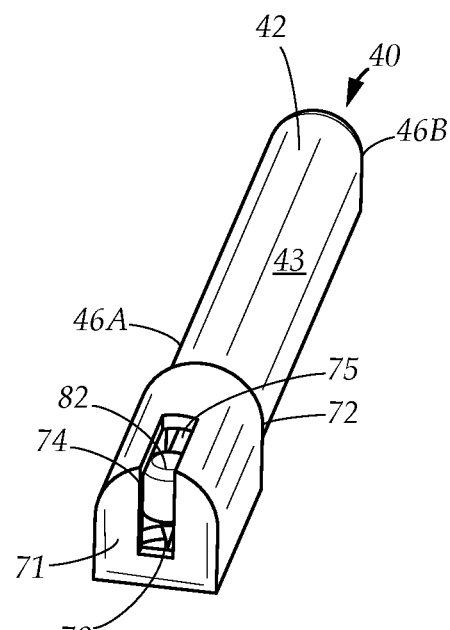
FIG. 3B is a diagrammatical perspective view of the detachable medication module from the needle housing first end, showing a needle head contained within the needle housing, and a needle actuation slot exposing the needle head, in accordance with an embodiment of the present disclosure.
Figure 3C:
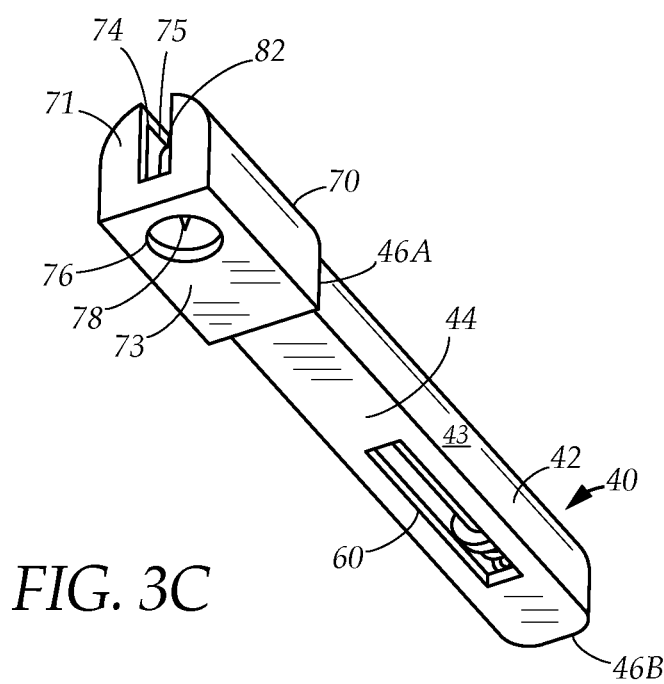
FIG. 3C is a diagrammatical perspective view of the detachable medication module from below, showing a needle opening, in accordance with an embodiment of the present disclosure.

Furthermore, referring to FIGS. 2A and 2C along with FIG. 4, the wearable medication injecting device 10 may have multiple attachment points arranged in parallel, such as a first attachment point 16A and a second attachment point 16B, each capable of engaging a separate detachable medication module 40. The medication reservoir 52 within each detachable medication module 40 may each contain a different medication, allowing for the simultaneous administering of a second medication 66 in addition to the first medication 64 by the wearable medication injecting device 10.

Returning to FIG. 2A, FIGS. 3A-C, FIG. 4, and FIG. 5C, the needle actuation mechanism 25 is adapted to apply downward pressure to the needle head 82 such that the needle 78 passes through the needle opening 76 as well as the injection aperture 32 of the mounting panel 14. In a preferred embodiment, the needle housing 70 has a needle actuation slot 74 which exposes the needle head 82 within the needle housing interior space 75. In a preferred embodiment, the needle actuation slot 74 is positioned at the needle housing first end 71. The needle actuation mechanism 25 has a needle actuation arm 27 adapted to pass through the needle actuation slot 74 to contact the needle head 82, as well as a needle actuation motor 26 adapted to selectively raise and lower the needle actuation arm 27. In certain embodiments, the needle housing 70 may include a return spring or other biasing element which causes the needle head 82 to return upwardly upon cessation of the downward pressure exerted by the needle actuation arm 27 against the needle head 82.

The injection actuation mechanism 55 is adapted to cause the injection plunger 56 to advance and deliver the medication 64 to the needle 78 via the medication transport line 54. In a preferred embodiment, the injection actuation mechanism 55 is aligned with the plunger actuation slot 60 when the detachable medication module 40 is engaged within the attachment point 16. The injection actuation mechanism 55 has a worm screw 30 arranged in parallel with the injection plunger 56, as well as an injection actuation motor 28 adapted to rotate the worm screw 30. The worm screw 30 has spiraling teeth 31 adapted to engage with the plunger flange 58C through the plunger actuation slot 60. Through the rotation of the worm screw 30 and the spiraling teeth 31, the plunger flange 58C is pushed towards the medication reservoir 52, causing the plunger head 58B to advance, expelling the medication 64 out of the medication reservoir 52. In certain embodiments, the plunger flange 58C may project through the plunger actuation slot 60 to engage with the worm screw 30. Furthermore, the detachable medication module may have a plunger spring 59 within the medication housing interior space 48 which establishes a biasing force between the plunger flange 58C and the medication housing second end 46A in order to prevent the injection plunger 56 from shifting as it advances and moves away from the medication housing second end 46A.

Referring to FIG. 4, In one embodiment, the detachable medication housing 42 may be adapted to accept a standard syringe 62 having a dispending end 62E, a syringe reservoir 62R and a syringe plunger 62P. The elongated shape of the detachable medication module 40 is adapted to accommodate placement of the syringe 62 within the medication housing interior space 48. The syringe reservoir 62R functions as the medication reservoir and contains the medication 64, while the syringe plunger 62P functions as the injection plunger 56 and also has a plunger flange 58C. The syringe 62 may be inserted into the medication housing interior space 48 with the dispensing end 62E towards the medication housing first end 46A such that the dispensing end 62E engages with the medication transport line 54 and the syringe plunger 62P is aligned with the plunger actuation slot 60, allowing the plunger flange 58C to engage with the worm screw 30.

Note that in certain embodiments, the injection actuation mechanism 55 may alternatively be implemented using an infusion pump or equivalent apparatus adapted to expel the medication 64 from the medication reservoir 52.

Referring to FIGS. 2A, FIGS. 3A-C, and FIG. 4, in a preferred embodiment, the wearable medication injecting device further has features adapted to ensure that the detachable medication module 40 remains secured within the attachment point 16 against unintended removal. The mounting panel upper face 14A may have a medication module retention hood 22 positioned thereon. The medication module retention hood 22 projects upwardly from the mounting panel upper face 14A and has a retention hood opening 24 adapted to receive the needle housing first end 71 of the detachable medication module 40. The attachment point 16 is elongated in shape to substantially match the dimensions of the medication housing shell 43, and further has an attachment recess 18 formed as a depression upon the mounting panel upper face 14A. The attachment recess 18 is adapted to enclose the medication housing bottom surface 44 while partially extending around the medication housing shell in an upward direction. The attachment recess 18 is positioned adjacent to the medication module retention hood 22 and extends away from the retention hood opening 24, allowing the needle housing first end 71 to be inserted into the retention hood opening 24 while the medication housing shell 43 is engaged with the attachment recess 18.

In a preferred embodiment, the needle actuation mechanism 25 is positioned within the medication module retention hood 22, and the needle actuation arm 27 is aligned with the needle actuation slot 74 of the needle housing 70. The injection aperture 32 is positioned upon the mounting panel 14 underneath the retention hood opening 24, and is adapted to align with the needle opening 76 on the needle housing bottom surface 73. The injection actuation mechanism 55 is positioned beneath the attachment recess 18, and the worm screw 30 projects upwardly to engage with the plunger flange 58C through the plunger actuation slot 60.

Referring now to FIGS. 5A-C, the needle 78 may be a subcutaneous needle adapted to penetrate the skin surface 154 in order to inject the medication 64 into subcutaneous tissue 155. Alternatively, the needle 78 may be replaced with a microneedle array 80 comprising a plurality of microneedles adapted to deliver the medication 64 via an intradermal injection. Note that the use of other types of needles 78 is contemplated herein, and a person of ordinary skill in the art in the field of the invention will appreciate that the needle head 82 may be adapted for other variations of needles 78 in a manner consistent with the principles of the present disclosure.

Figure 6A:
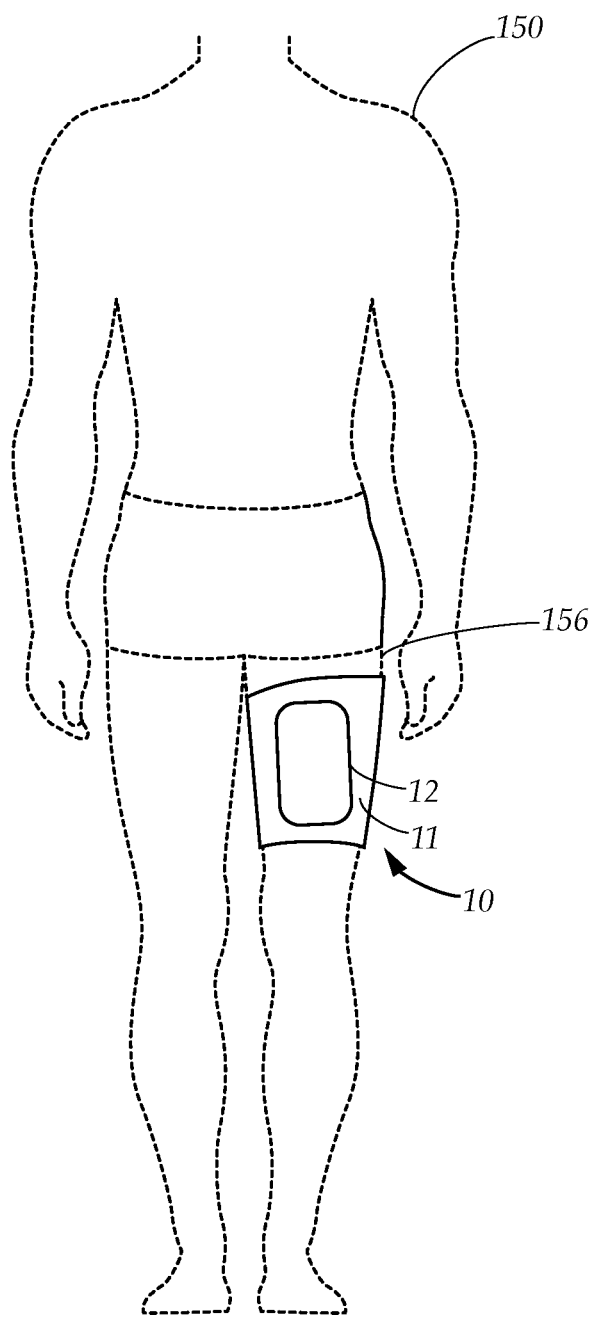
FIG. 6A is a diagrammatical front view of a patient wearing the wearable medication injecting device around the patient's thigh, in accordance with an embodiment of the present disclosure.
Figure 6B:
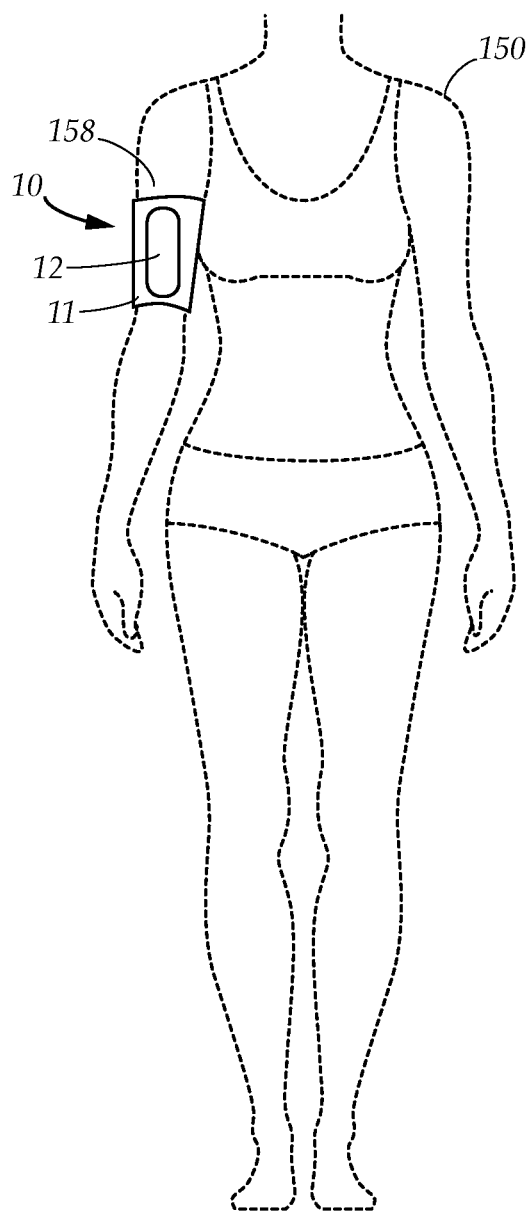
FIG. 6B is a diagrammatical front view of a patient wearing the wearable medication injecting device around the patient's upper arm, in accordance with an embodiment of the present disclosure.

Referring now to FIG. 1 and FIGS. 6A-B, the wearable medication injecting device 10 may be worn at different parts of the patient's body suitable for intradermal or subcutaneous injections. For example, the wearable medication injection device 10 may be worn around one of the patient's limbs, such as the upper thigh 156, the forearm 152, or the upper arm 158. The band 11 may be adjustable, and the elasticity of the band 11 allows the medication injection assembly 12 to be secured against any limb of the patient 150.

Figure 7B:
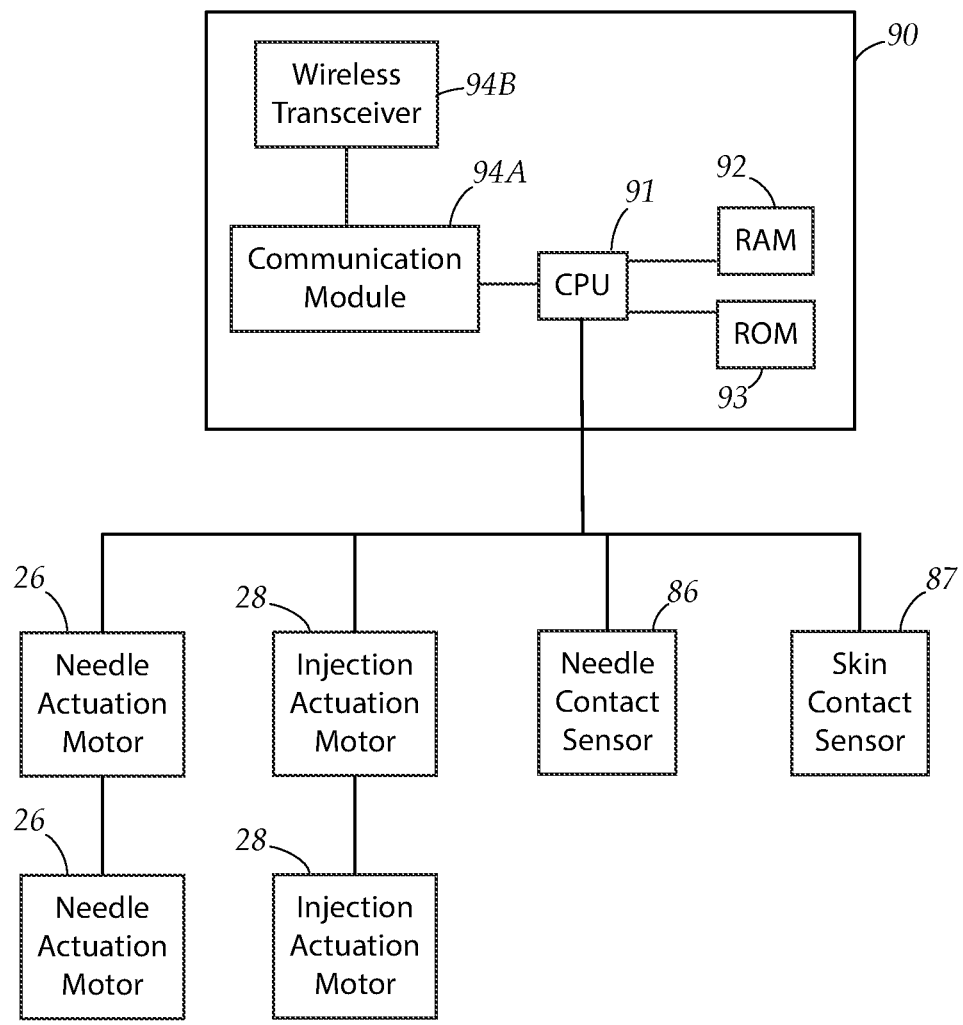
FIG. 7B is a block diagram depicting a device control module adapted to control the functions of the wearable medication injecting device, in accordance with an embodiment of the present disclosure.
Figure 8A:
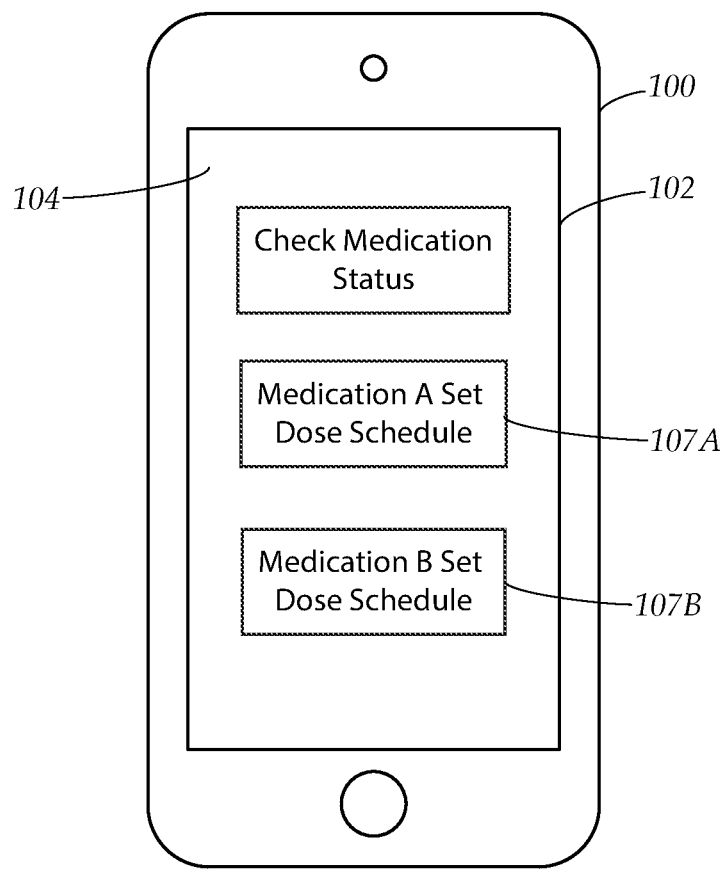
FIG. 8A is a diagrammatical front view of the user control device, showing a control application which allows a user to set a dose schedule, in accordance with an embodiment of the present disclosure.
Figure 8B:
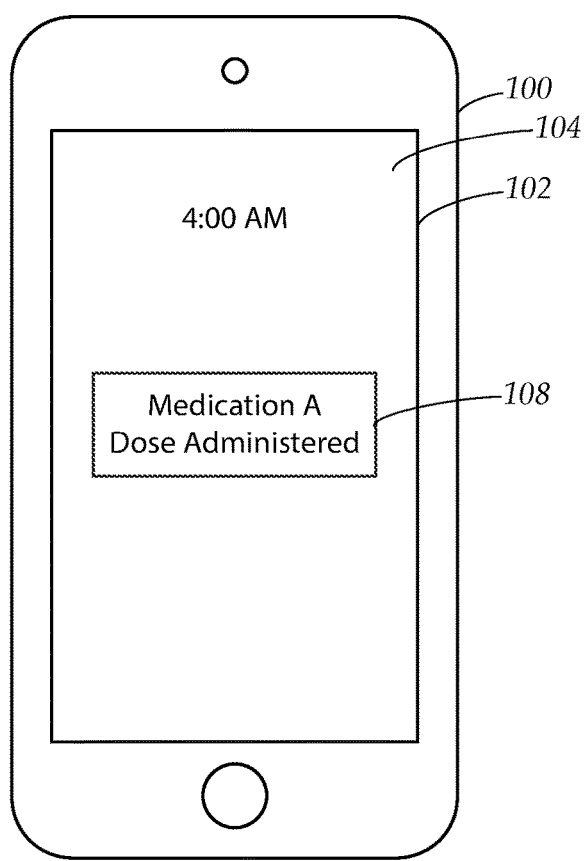
FIG. 8B is a diagrammatical front view of the user control device, showing a dose administered alert informing the user that a scheduled dose has been administered to the patient, in accordance with an embodiment of the present disclosure.
Figure 8C:
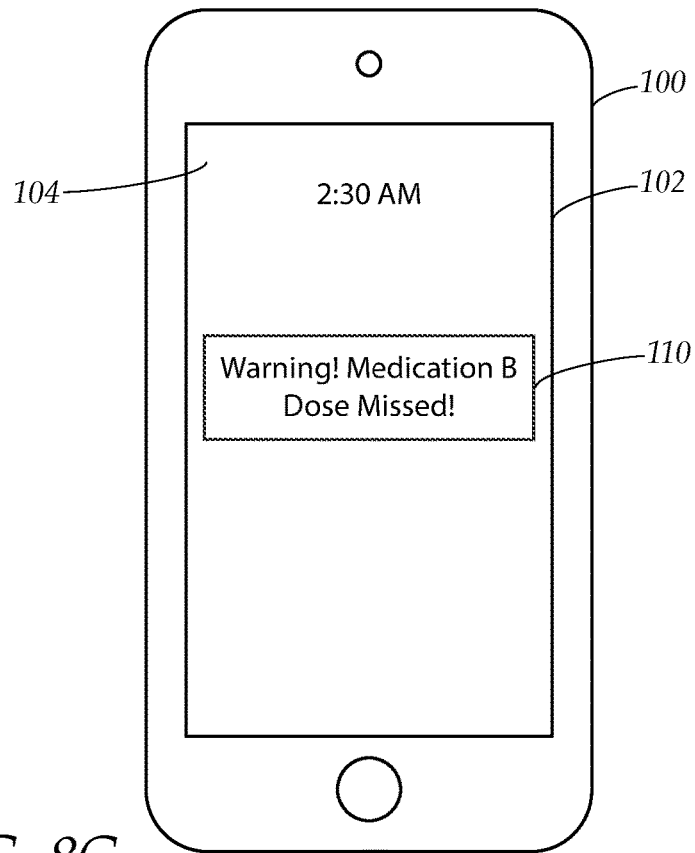
FIG. 8C is a diagrammatical front view of the user control device, showing a missed dose alert informing the user that a scheduled dose has not been successfully administered to the patient, in accordance with an embodiment of the present disclosure.
Figure 8D:
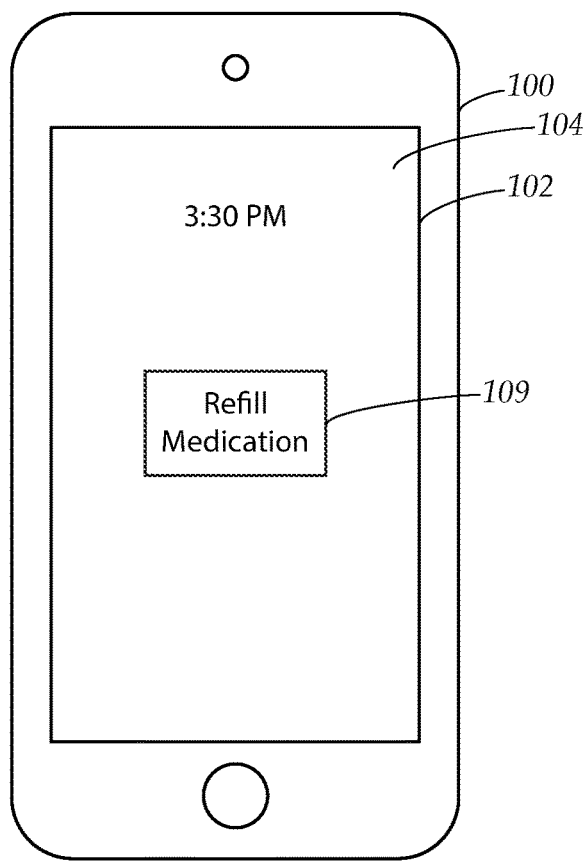
FIG. 8D is a diagrammatical front view of the user control device, showing a refill medication alert informing the user that the medication has been depleted, in accordance with an embodiment of the present disclosure.
Figure 8E:
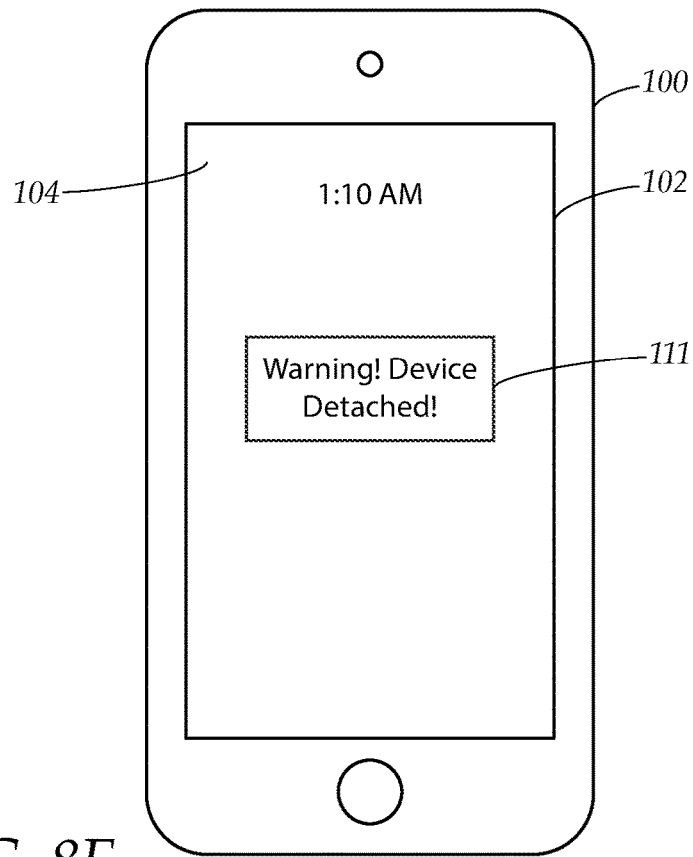
FIG. 8E is a diagrammatical front view of the user control device, showing a device detached alert informing the user that the wearable medication injecting device is no longer properly attached to the patient, in accordance with an embodiment of the present disclosure.

Turning now to FIGS. 7A-B while also referring to FIG. 1, the wearable medication injection device 10 further comprises a device control module 90. In a preferred embodiment, the device control module 90 is positioned within the mounting panel 14, and is adapted to control the functions of the wearable medication injecting device 10. The device control module 90 may be implemented using a microcontroller, system on a chip, or a functional equivalent as will be apparent to a person of ordinary skill in the art in the field of the invention. The device control module 90 has a CPU 91, a RAM 92, and a ROM 93, and is adapted to control the operation of the needle actuation motor 26 and the injection actuation motor 28. The device control module 90 further has a communication module 94A adapted for wireless data communication and a wireless transceiver 94B adapted to transmit and receive wireless signals, allowing the device control module 90 to communicate wirelessly with the user control device 100. Communication between the device control module 90 and the user control device 100 may be implemented using a wireless communication protocol such as Bluetooth, or other form of RF communication, as will be apparent to a person of ordinary skill in the art in the field of the invention.

The user control device 100 may be a smartphone, tablet, personal computer, or other computing device which has a device screen 102 and is adapted to communicate wirelessly with the wearable medication injecting device 10 via the device control module 90. In a preferred embodiment, the user control device 100 transmits a control signal 95 to the wearable medication injecting device 10 to initiate an injection by activating the needle actuation motor 26 and the injection actuation motor 28 as appropriate. Referring to FIGS. 8A-E while also referring to FIG. 2C, FIG. 4, and FIGS. 7A-B, a control application 104 implemented using the user control device 100 allows a user to control the wearable medication injecting device 10 via a graphical user interface presented on the device screen 102. The user may be the patient, or another person overseeing the care of the patient. The control application 104 allows the user to define 107A a dose schedule which determines a dose time and a dose amount for the medication 64. The user may also define a second dose schedule 107B for the administering of the second medication 66. Once the dose schedule has been defined, the wearable medication injecting device 10 will automatically initiate a scheduled injection at the defined dose time containing the dose amount of the medication 64. The dose time may comprise times at which the scheduled injections will occur, or time intervals between scheduled injections, with the second medication being administered at one or more second medication dose times, at a second medication dose amount. In a preferred embodiment, the dose schedule is monitored by the control application 104, and each scheduled injection is initiated upon transmission of the control signal 95 by the user control device 100. In certain embodiments, the device control module 90 may be adapted to independently execute the medication schedule and initiate the scheduled injections according to the dose schedule and the defined dose amounts.

The device control module 90 may be adapted to transmit a status signal 96 to the user control device 100 to convey information regarding a device status of the wearable medication injecting device 10. For example, the device control module 90 may be adapted to detect whether a scheduled injection failed or was successfully administered, whether the medication 64 within the medication reservoir 52 is depleted, and/or whether the wearable medication injecting device 10 is properly attached to the patient or if it is detached. Any of the aforementioned device statuses may be conveyed to the user control device 100 via the status signal 96.

The user control device 100 may alert the user to any of the device statuses via the control application 104. For example, the control application 104 may present a dose administered alert 108 to the user. Alternatively, a missed dose alert 110 may be presented to the user if a scheduled injection is not successfully administered or if the status signal indicating successful administering of the scheduled injection is not received. Similarly, the control application 104 may present a refill alert 109 to the user once the medication 64 is depleted, and a detached device alert 111 informing the user that the wearable medication injecting device 10 is detached from the patient 150.

Referring to FIG. 2C, FIG. 4, FIGS. 7A-B, and FIG. 8A, where the second medication 66 is in use, the device control module 90 and the user control device 100 are adapted to execute the dose schedule and second dose schedule simultaneously. The device control module 90 is further adapted to select the appropriate detachable medication module 40 in order to administer either the medication 64 or the second medication 66 as appropriate. In one embodiment, each attachment point 16 may be distinguished by a number or other identifier, and the user may enter the formulation of the medication within the detachable medication module 40 engaged with each attachment point 16 using the control application 104. For example, the first medication 64 may be contained in a first detachable medication module 40A engaged within the first attachment point 16A, while the second medication 66 may be stored within a second detachable medication module 40B engaged within the second attachment point 16B.

Referring to FIG. 2B, FIG. 4, FIG. 5C, and FIGS. 7A-B, the wearable injecting device 10 may have various sensors which allow the device control module 90 to determine the device status. The mounting panel inner face 14B may have a device contact sensor 87 positioned thereon which is adapted to detect whether the wearable medication injecting device 10 is properly attached to the patient 150. Similarly, the needle head 82 may have a needle contact sensor 86 adapted to detect contact with the skin surface 154 of the patient once the needle 78 has penetrated the skin surface 154. For example, the needle head 82 may have a top portion 82T and a bottom portion 82B. The needle extends downwardly away from the bottom portion 82B. The needle contact sensor 86 may be positioned on the bottom portion 82B around the needle 78 in order to contact the skin surface 154 once the needle 78 has penetrated the skin surface 154 to a sufficient depth to reach the subcutaneous tissue 155. The device contact sensor 87 and the needle contact sensor 86 may be implemented using capacitive sensors or other sensor technology as will be appreciated by a person of ordinary skill in the art in the field of the invention. A flow sensor 88 may be positioned to detect the flow of the medication 64 through the medication transport line 54. A successful scheduled injection may be detected by first determining whether the needle 78 has penetrated the skin surface 154 using the needle contact sensor 86, followed by detecting whether the medication 64 is successfully injected using the flow sensor 88. The device control module 90 may also determine whether the medicine in the medication reservoir 52 has been depleted. In certain embodiments, the medication reservoir 52 may contain sufficient medication 64 for a defined number of doses. The injection plunger 56 may be advanced a set distance sufficient to expel only enough medication 64 to equal the dose amount, and the device control module 90 may be adapted to record the remaining doses remaining within the medication reservoir 52.

Alternatively, where it is desirable to replace the needle 78 after each injection, the medication reservoir 52 may contain only a single dose, requiring the replacement of the detachable medication module 40 after each scheduled injection performed using said detachable medication module 40. Attaching multiple detachable medication modules 40 to the mounting panel 14 allows one scheduled injection to be administered for each of the detachable medication modules 40 before the supply of medication is depleted. Furthermore, each needle 78 is used only once, ensuring that each scheduled injection is performed using a clean needle 78.

Figure 9:
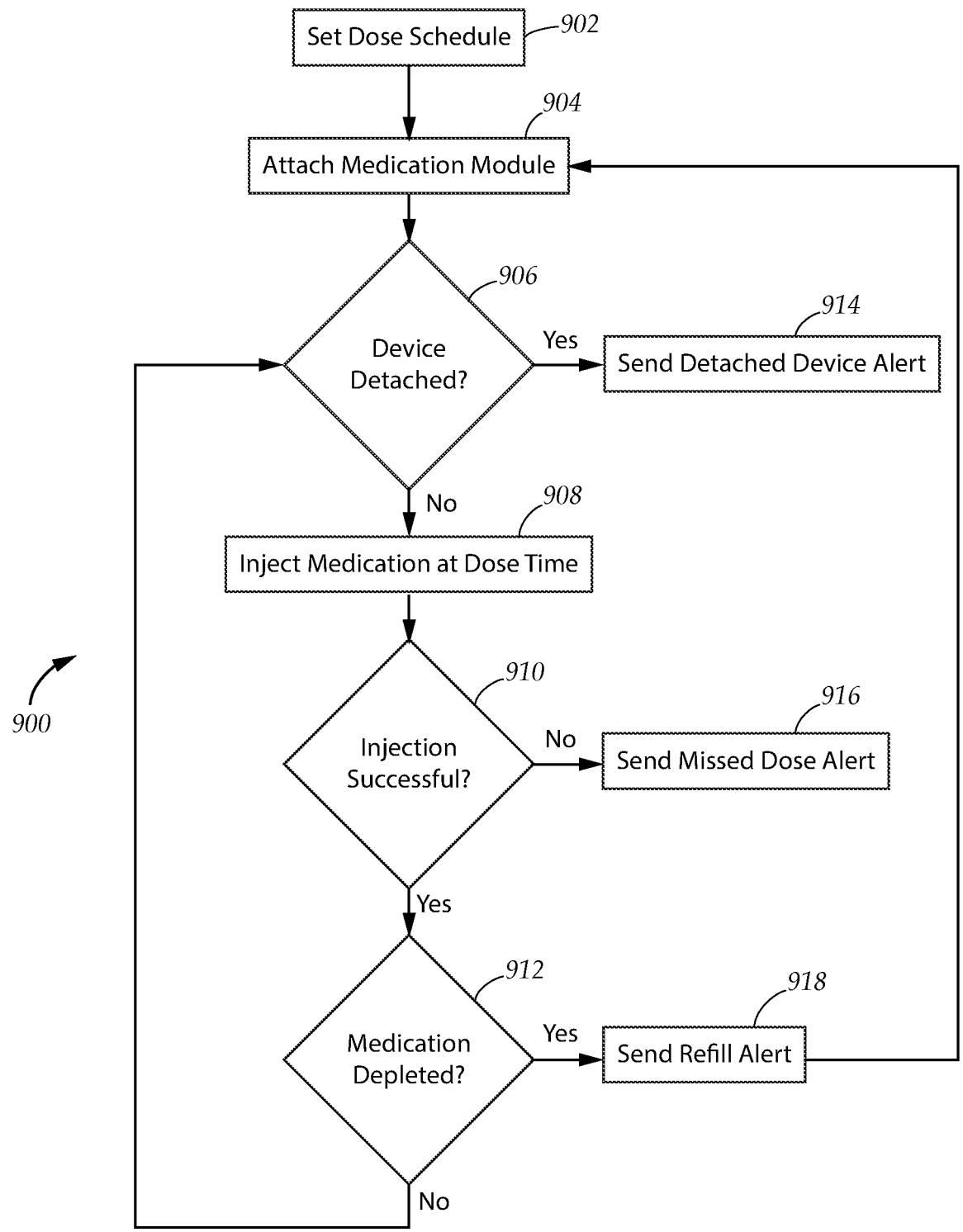
FIG. 9 is a flowchart depicting an exemplary medication injection process illustrating the operation of the wearable medication injecting device, in accordance with an embodiment of the present disclosure.

Turning now to FIG. 9 while also referring to FIGS. 2A-B, FIG. 4, FIG. 5C, FIG. 7A, and FIGS. 8A-E, an example medication administering process 900 depicting the operation of the wearable medication injecting device 10 is shown. First, at step 902, the user defines 107A the dose schedule using the user control device 100, by inputting the dose time and the dose amount for each scheduled injection. Next, at step 904, the wearable medication injecting device 10 is prepared for use. The detachable medication module 40 is detachably engaged within the attachment point 16, and the wearable medication injecting device 10 is attached to the one of the patient's limbs such that mounting panel inner face 14B contacts the patient's skin surface 154 and the medication injection assembly 12 is held in place by the band 11. Once the wearable medication injecting device 10 is in place, the user control device 100 will begin execution of the dose schedule. The device control module 90 begins monitoring the device status and will convey the device status to the user control module 100 via a status signal 96. At step 906, if the device contact sensor 87 determines that the mounting panel inner face 14B has been detached from the patient's skin surface 154, the control application 104 will then present the user with a detached device alert 111 at step 914. At step 908, once the dose time occurs, the user control device 100 will transmit a control signal 95 to the device control module 90 to initiate the scheduled injection. Next, the device control module 90 determines whether the scheduled injection was successfully administered at step 910 using the needle contact sensor 86 and the flow sensor 88. For example, the needle contact sensor 86 may determine whether the needle 78 successfully penetrated the skin surface 154, while the flow sensor 88 may indicate whether the amount of injected medication 64 matches the dose amount. If the scheduled injection is determined to have been unsuccessful, the device control module 90 will convey the device status to the user control device 100, and the control application 104 will present the user with a missed dose alert 110 at step 916. Next, the device control module 90 will determine if the medication 64 has been depleted at step 912. If the medication 64 is depleted, the control application 104 will present the user with a refill alert at step 918. Otherwise, the process returns to step 906. Note that the precise order of the steps in the example medication administering process 900 is not intended to be limiting, and individual steps may be varied or substituted while remaining in adherence with the principles of the present disclosure.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate or transport a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. Other types of languages include XML, XBRL and HTML5. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. Each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments of the present disclosure. In this regard, each block in the flowchart or block diagrams may represent a module, segment or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The flow diagrams depicted herein are just one example. There may be many variations to this diagram or the steps (or operations) described therein without departing from the spirit of the disclosure. For instance, the steps may be performed in a differing order and/or steps may be added, deleted and/or modified. All of these variations are considered a part of the claimed disclosure.

In conclusion, herein is presented a wearable medication injecting device. The disclosure is illustrated by example in the drawing figures, and throughout the written description. It should be understood that numerous variations are possible, while adhering to the inventive concept. Such variations are contemplated as being a part of the present disclosure.

What is claimed is:

1. A wearable medication injecting device for administering a medication to a patient, the patient having a limb and a skin surface, comprising:
   a detachable medication module having a medication housing, the medication housing having a medication housing first end, a medication housing interior space, and a medication housing second end, the detachable medication module further having a medication reservoir contained within the medication housing interior space adapted to store the medication, and a needle housing attached to the medication housing first end, the needle housing having a needle head movably engaged therein, the needle head is adapted to move vertically and has a needle which projects downwardly from the needle head and is adapted to penetrate the skin surface and deliver the medication therethrough, the detachable medication module further having a medication transport line adapted to transport the medication from the medication reservoir to the needle;
   a medication injection assembly having a mounting panel having an upper face and an inner face adapted to be positioned against the skin surface, the mounting panel further having an injection aperture extending between the upper face and the inner face of the mounting panel, and an attachment point disposed on the upper face adapted to allow the detachable medication module to be detachably secured within, the medication injection assembly further having a needle actuation mechanism adapted to push the needle head downwardly and lower the needle towards the skin surface through the injection aperture, and an injection actuation mechanism adapted to expel the medication from the medication reservoir;
   an elastic band adapted to secure the medication injection assembly in place against the limb;
   a device control module adapted to control the needle actuation mechanism and the injection actuation mechanism, the device control module further having a wireless transceiver adapted for wireless communication; and
   a user control device adapted to communicate wirelessly with the device control module and initiate a scheduled injection according to a dose schedule.

2. The wearable medication injecting device described in claim 1, the detachable medication module further having an injection plunger with a plunger head, a circular plunger flange extending towards the medication housing second end, and a plunger shaft therebetween, the plunger head is adapted to advance within the medication reservoir to expel the medication stored within.

3. The wearable medication injecting device described in claim 2, wherein the injection actuation mechanism is adapted to engage with the plunger flange while the detachable medication module is engaged within the attachment point, and advance the injection plunger by pushing the plunger flange towards the medication housing first end.

4. The wearable medication injecting device described in claim 3, wherein:
   the needle actuation mechanism has a needle actuation arm adapted to selectively raise and lower, whereby the needle is lowered through the injection aperture by the needle actuation arm contacting and pushing the needle head downwardly; and
   the needle housing further has a biasing element which causes the needle head to return upwardly upon cessation of downward pressure upon the needle head from the needle actuation arm.

5. The wearable medication injecting device described in claim 4, wherein the mounting panel further has a retention hood having a retention hood opening positioned upon the upper face adjacent to the attachment point, the retention hood opening is adapted to receive the needle housing when the detachable medication module is engaged within the attachment point.

6. The wearable medication injecting device described in claim 5, wherein the attachment point has an attachment recess formed as a depression upon the upper face of the mounting panel, the attachment recess extends away from the retention hood opening and is adapted to engage a medication housing shell once the detachable medication module is engaged within the attachment point.

7. The wearable medication injecting device described in claim 6, wherein:
   the medication injection assembly further has a needle contact sensor adapted to detect penetration of the skin surface by the needle; and
   the user control device is adapted to present a user with a missed dose alert upon the needle contact sensor failing to detect the penetration of the skin surface at the dose time.

8. The wearable medication injecting device as described in claim 7, wherein:
   the inner face of the mounting panel further has a skin contact sensor adapted to determine whether the inner face is attached to or detached from the skin surface; and
   the user control device is adapted to present the user with a detached device alert upon the device control module detecting detachment of the inner face from the skin surface.

9. The wearable medication injecting device as described in claim 8, further comprising:
   a second detachable medication module adapted to engage with a second attachment point positioned on the upper face of the mounting panel, the second detachable medication module is adapted to contain a second medication, whereby the second medication is administered in accordance with a second dose schedule.

10. A wearable medication injecting device for administering a medication to a patient, the patient having a limb and a skin surface, the medication is stored within a syringe having a dispensing end, a medication reservoir for containing the medication, and an injection plunger adapted to advance and expel the medication through the dispensing end, the syringe plunger further having a circular plunger flange, the wearable medication injecting device comprising:
- a detachable medication module having a medication housing, the medication housing having a medication housing first end, a medication housing second end, an elongated medication housing shell extending therebetween, and a medication housing interior space adapted to receive the syringe, the detachable medication module further having a needle housing attached to the medication housing first end, the needle housing having a needle head movably engaged therein, the needle head is adapted to move vertically and has a needle which projects downwardly from the needle head and is adapted to penetrate the skin surface and deliver the medication therethrough, the detachable medication module further having a medication transport line positioned at the medication housing first end adapted to engage with the dispensing end of the syringe and transport the medication from the medication reservoir to the needle;
- a medication injection assembly having a mounting panel having an upper face and an inner face adapted to be positioned against the skin surface, the mounting panel further having an injection aperture extending between the upper face and the inner face of the mounting panel, and an attachment point disposed on the upper face adapted to allow the detachable medication module to be detachably secured within, the medication injection assembly further having a needle actuation mechanism adapted to push the needle head downwardly and lower the needle towards the skin surface through the injection aperture, and an injection actuation mechanism adapted to advance the injection plunger to expel the medication from the medication reservoir through the medication transport line;
- an elastic band adapted to secure the medication injection assembly in place against the limb;
- a device control module adapted to control the needle actuation mechanism and the injection actuation mechanism, the device control module further having a wireless transceiver adapted for wireless communication; and
- a user control device adapted to communicate wirelessly with the device control module and initiate a scheduled injection according to a dose schedule.

11. The wearable medication injecting device as described in claim 10, wherein:
- the medication housing shell having a medication housing bottom surface wherein the medication housing bottom surface has a plunger actuation slot which exposes the injection plunger; and
- the injection actuation mechanism has a worm screw with spiraling teeth, and an injection actuation motor adapted to rotate the worm screw, the worm screw is adapted to engage with the plunger flange through the plunger actuation slot while the detachable medication module is engaged within the attachment point, whereby the worm screw is adapted to advance the injection plunger by pushing the plunger flange towards the medication housing first end.

12. The wearable medication injecting device as described in claim 11, wherein:
- the needle actuation mechanism has a needle actuation arm adapted to selectively raise and lower, whereby the needle is lowered through the injection aperture by the needle actuation arm contacting and pushing the needle head downwardly; and
- the needle housing further has a biasing element which causes the needle head to return upwardly upon cessation of downward pressure upon the needle head from the needle actuation arm.

13. The wearable medication injecting device as described in claim 12, wherein:
- the mounting panel further has a retention hood having a retention hood opening positioned upon the upper face adjacent to the attachment point, the retention hood opening is adapted to receive the needle housing when the detachable medication module is engaged within the attachment point; and
- the attachment point has an attachment recess formed as a depression upon the upper face of the mounting panel, the attachment recess extends away from the retention hood opening and is adapted to engage the medication housing shell by enclosing the medication housing bottom surface and partially extending upwardly around the medication housing shell.

14. The wearable medication injecting device as described in claim 13, further comprising:
- a needle contact sensor adapted to detect penetration of the skin surface by the needle; and
- a control application implemented on the user control device, adapted to allow a user to define the dose schedule, and present the user with a missed dose alert upon the needle contact sensor failing to detect the penetration of the skin surface at the dose time.

15. A method for administering a medication to a patient, the patient having a limb and a skin surface, the method comprising the steps of:
- providing a wearable medication injecting device comprising:
  - a detachable medication module having a medication housing and a needle housing, the medication housing containing a medication reservoir adapted to store the medication, the needle housing is attached to the medication housing, and contains a needle head movably engaged therein, the needle head has a needle which projects downwardly from the needle head and is adapted to penetrate the skin surface of the patient and deliver the medication therethrough;
  - a medication injection assembly having a mounting panel with an upper face, an inner face, an injection aperture extending between the upper face and the inner face, and an attachment point positioned upon the upper face, the attachment point is adapted to allow the detachable medication module to be detachably engaged therein, the medication injection assembly further having a needle actuation mechanism adapted to lower the needle to penetrate the skin surface, and an injection actuation mechanism adapted to expel the medication from the medication reservoir;
  - a device control module adapted to control the needle actuation mechanism and the injection actuation mechanism, the device control module further having a wireless transceiver adapted for wireless communication;
  - an elastic band adapted to secure the medication injection assembly in place against the limb; and
  - a user control device adapted to communicate wirelessly with the device control module;

defining a dose schedule by a user using the user control device, whereby the dose schedule contains a dose time for administering the medication to the patient via a scheduled injection;

engaging the detachable medication module within the attachment point, orienting the needle housing toward the needle actuation mechanism, and aligning the needle with the injection aperture of the mounting panel;

pressing the inner face of the mounting panel against the skin surface of the patient, and securing the wearable medication injecting device to the limb of the patient using the band;

executing the dose schedule using the user control device; and performing a scheduled injection upon occurrence of the dose time, transmitting a control signal to the device control module, pushing the needle head downwardly and vertically using the needle actuation mechanism, causing the needle to pass through the injection aperture and penetrate the skin surface, and delivering the medication to the patient through the needle.

16. The method as described in claim 15, wherein:
the step of performing a scheduled injection upon occurrence of the dose time, is followed by the step of:
removing the detachable medication module from the attachment point upon depletion of the medication within the medication reservoir, and replacing the detachable medication module with a new detachable medication module.

17. The method as described in claim 16, wherein:
the detachable medication module further has an injection plunger adapted to advance and expel the medication from the medication reservoir, the injection plunger having a circular flange;
the injection actuation mechanism is adapted to engage with the flange and advance the injection plunger;
the step of engaging the detachable medication module within the attachment point further comprises the step of aligning the injection actuation mechanism with the flange of the injection plunger; and the step of performing a scheduled injection upon occurrence of the dose time further comprises the step of pushing the flange using the injection actuation mechanism to advance the injection plunger.

18. The method as described in claim 17, wherein:
the needle actuation mechanism has a selectively lowerable needle actuation arm adapted to push the needle head downwardly towards the injection aperture;
the needle housing further has a biasing element;
the step of performing a scheduled injection upon occurrence of the dose time further comprises the step of lowering the needle actuation arm to contact and push the needle head towards the injection aperture; and
the step of performing a scheduled injection is followed by the step of raising the needle actuation arm and returning the needle head upwardly using the biasing element upon cessation of downward force exerted by the needle actuation arm.

19. The method as described in claim 18, wherein:
the detachable medication module further has a needle contact sensor adapted to detect penetration of the skin surface by the needle; and
the step of performing a scheduled injection upon occurrence of the dose time is followed by the step of:
determining the success or failure of the scheduled injection using the needle contact sensor, and presenting the user with a missed dose alert via the user control device upon the needle contact sensor failing to detect the penetration of the skin surface at the dose time.

20. The method as described in claim 19, wherein:
the medication injection assembly further has a skin contact sensor positioned upon the inner face of the mounting panel, the skin contact sensor is adapted to determine whether the inner face is attached or detached from the skin surface; and
further the step of:
detecting detaching of the inner face from the skin surface using the skin contact sensor, and presenting the user with a detached device alert via the user control device.

* * * * *